United States Patent [19]

Leshchiner et al.

[11] Patent Number: 4,795,741

[45] Date of Patent: Jan. 3, 1989

[54] COMPOSITIONS FOR THERAPEUTIC PERCUTANEOUS EMBOLIZATION AND THE USE THEREOF

[75] Inventors: Adolf Leshchiner, Fairview, N.J.; Nancy E. Larsen, Southfield, N.Y.; Endre A. Balazs, Ft. Lee; Sadek K. Hilal, Englewood Cliffs, both of N.J.

[73] Assignee: Biomatrix, Inc., Ridgefield, N.J.

[21] Appl. No.: 47,419

[22] Filed: May 6, 1987

[51] Int. Cl.[4] .................... C08F 8/00; C08G 79/08
[52] U.S. Cl. ........................ 514/21; 514/781; 524/17; 524/27; 524/29; 536/4.1
[58] Field of Search ............ 514/21, 781; 524/17, 524/29, 27; 536/4.1

[56] References Cited

U.S. PATENT DOCUMENTS 4,582,865  4/1986  Balazs et al. ................... 524/27

OTHER PUBLICATIONS

Taki et al "Balloon Embolization of a Giant Aneurysm Using a Newly Developed Catheter" *Surg. Neurol.* vol. 12, 363-365, Nov. 1979.

Taki et al "Radipaque Solidifying Liquids for Releasable Balloon Technique: A Technical Note" *Surg. Neurol.*, vol. 13, 140-142, Feb. 1980.

*Primary Examiner*—John Kight
*Assistant Examiner*—Nathan M. Nutter
*Attorney, Agent, or Firm*—Sheldon Palmer

[57] ABSTRACT

Percutaneous emboli are formed for therapeutic and/or corrective reasons by using a composition which includes crosslinked gels of hyaluronic acid (HA), hylan (HY) or mixed crosslinked gels of HA or HY with other materials, thrombin and cationic substances containing quaternary ammonium groups. Other optional materials include fillers and radio-opaque substances.

29 Claims, 1 Drawing Sheet

COMPOSITIONS FOR THERAPEUTIC PERCUTANEOUS EMBOLIZATION AND THE USE THEREOF

BACKGROUND OF THE INVENTION

1. Field of the Invention

The invention relates to novel compositions for use in effecting therapeutic percutaneous embolization, and more particularly, to compositions for the embolization of blood vessels. The invention also relates to embolization methods using the above compositions.

2. Prior Art

Therapeutic percutaneous embolization has been proven to be an effective tool in managing various disorders such as vascular lesions, aneurysms, and arteriovenous malformations. This technique is also very effective in treating tumors by the careful and selective obliteration of the arterial supply of neoplasms where such blood vessels enter the tumor and bring it the nutrients which it requires. Percutaneous embolization has also been known to be a lifesaving procedure in certain cases of arteriovenous malformations.

Several methods have heretofore been proposed for performing percutaneous embolization. Thus, a balloon embolization technique was developed according to which a catheter with a balloon at its end was used (W. Taki et al, Surg. Neurol. 12, p.p. 363–365, 1979; G. Deburn et al, J. Neurosurg., 1978, p.p. 635–649). According to this technique, the catheter must be flexible enough to be introduced into arteries of complex configuration. The inflatable balloon is attached to the catheter through a specially designed joint which is twisted off when the inflated balloon is in the target area, i.e., the vascular lesion which is the aim of the treatment. The released balloon then seals off the blood vessel itself. The disadvantage of this method is that the sealing lasts only for a few days because the balloon eventually deflates.

Another method for embolization was proposed according to which a liquid containing a readily polymerizable monomer and a catalyst for the polymerization is introduced through the catheter into the balloon. It was suggested to use 2-hydroxyethyl methacrylate (HEMA) as the monomer. (W. Taki, et al, Surg. Neurol. 13, p.p. 140–142 (1980)). The disadvantages associated with this method are the difficulty in monitoring the proper volume of liquid supplied to the balloon so as to have an adequate embolization occur; and the possibility of polymerization occurring in the catheter (as opposed to the blood vessel) which would result in failure of the entire procedure.

Another quite efficient embolization method was suggested, according to which radioopaque Silastic ® spheres are used to occlude blood vessels. (S. K. Hilal et al, J. of Neurosurg. 43, p.o. 275–287 (1975)). Depending upon the precise nature of the case, and the blood vessel characteristics, the number of spheres required ranged from 30 to 250 and varied from 1 mm to 2.5 mm in diameter. The spheres are delivered through a catheter by a special device and at all times are immersed in a sterile physiological solution. Though providing adequate and long lasting embolization, this system has several drawbacks. A large amount of fluid is required for injection which can be a limiting factor in some cases and, in addition, the embolization procedure is long and only one or two vessels can be occluded in any one day.

Cross-linked gels of hyaluronan (also and formerly known as hyaluronic acid) are known, and their preparation is described in U.S. Pat. Nos. 4,582,865; 4,605,691 and 4,636,524. In addition, the slightly modified hyaluronan known as hylan is described in published U.K. application No. 2,172,295A.

SUMMARY OF THE INVENTION

Figure 1:
FIG. 1 is a photograph showing the arterially injected ears of a rabbit one week after injection with a composition according to the invention.

In one aspect, the invention provides compositions for effecting therapeutic percutaneous embolization, i.e., the intentional formation of emboli.

In another aspect, the invention provides viscoelastic and pseudoplastic compositions for effecting therapeutic percutaneous embolization.

In yet another aspect, the invention provides compositions for effecting permanent percutaneous embolization and which do not cause undesirable reactions in the surrounding tissues.

In still another aspect, the invention provides methods for performing percutaneous embolization for therapeutic purposes using the instant compositions.

DESCRIPTION OF THE PREFERRED EMBODIMENT

The present invention is based upon our discovery that (1) cross-linked gels of hyaluronic acid, or hyaluronan, according to the nomenclature recently suggested (E. A. Balazs et al, Biochem. J. letters, 235 [3], p. 903 (1986)), and hereinafter referred to as HA, (2) cross-linked gels of the slightly modified hyaluronic acid known as hylan (UK patent application GB No. 2,172,295A) hereinafter referred to as HY, or (3) mixed crosslinked gels of HA and/or HY with other polymers and low molecular weight substances can be conveniently used as a base for compositions which provide fast, reliable therapeutically motivated embolizations.

The above mentioned gels are described (and claimed) in U.S. Pat. Nos. 4,582,865 and 4,605,691, both owned by the assignee hereof. The main features of these gels are their ability to swell in aqueous media to a very high degree, general biological inertness and unusual rheological properties which can be modified to any desirable combination by changing selected parameters in the preparation of the gels. In general, the rheological properties of the gels fall within the following range: apparent viscosity n at low shear rate ($\gamma = 0.01 \text{th s}^{-1}$) from 10 to 10,000 Pa.s; dynamic storage modulus G', which characterizes the elastic properties of the material, at relatively high frequency (5 Hz) of from 1 to 500 Pa and even higher; dynamic loss modulus which reflects viscous behavior of from 1 to 200 Pa (5 Hz frequency). The most important property of these gels for the purposes of the present invention is their shear dependent plasticity which can easily be varied from 10 to 10,000 (shear dependent plasticity is stated as the ratio of the apparent viscosities of the gel measured at two different shear rates $\gamma = 0.01$ and $14.7 \text{s}^{-1}$). This shear dependent plasticity enables one to "push"

the viscoelastic compositions according to the invention through the small diameter catheters that were usually used in percutaneous embolization.

As is taught in the above mentioned U.S. patents, the cross-linked viscoelastic gels can consist of pure HA or HY or HA and/or HY co-cross-linked with other polymers including other glycosaminoglycans such as chondroitin sulfate, heparin, keratin sulfate and so on, proteins such as collagen, albumin and others, cellulose derivatives such as carboxymethylcellulose, hydroxyethylcellulose, ethylcellulose and other synthetic water-soluble polymers containing chemical entities like hydroxy, amino or sulfhydryl groups reactive towards the cross-linking agent divinyl sulfone. The cross-linked viscoelastic gels can also contain a variety of low molecular weight substances attached through the cross-linking agent to polymeric chains of HA or HY or other polymers. Examples of these low molecular weight substances are drugs and other biologically active substances, dyes, amino acids, peptides and so on.

In addition to the cross-linked viscoelastic gels, the compositions according to the present invention may also contain water-insoluble fillers which can be a hydrophillic, hydrophobic inorganic or organic material.

Examples of such inorganic materials are metal powders, finely dispersed silica, insoluble salts such as barium sulfate. Examples of organic fillers are finely dispersed polymers such as microcrystalline cellulose, polyethylene, polytetrafluoroethylene, cross-linked polymers such as cross-linked hyaluronic acid, agarose, ion-exchange resins and the like. By adjusting the amount of the filler one can easily modify the rheological properties of the composition and affect the hardness of the clot formed upon contact of the composition with blood. Some of these fillers, for example tantalum powder or barium sulfate, serve as a radio-opaque agent which provides valuable X-ray visualization during the embolization procedure, and can enable the surgeon to monitor the procedure while it is being performed. Others, like ion-exchange resins, can affect the blood clot formation and will be discussed below in more detail. Depending upon the nature of the filler and its function, the content of the filler in the composition according to the invention is generally from 1 to 60 wt. % based on the whole composition, preferably from 2 to 30 wt. %, and most preferably from 5 to 25 wt. %.

Another component of the composition of the present invention is a cationic organic substance containing quaternary ammonium groups. This substance can be a monomeric compound containing one or several cationic groups, for example choline chloride; acetylcholine chloride; N,N,N,N',N',N'-hexamethyl-1,6-diaminium bromide; or low molecular weight polymers such as hexadimethrine bromide or soluble high molecular weight polymers, either synthetic or those obtained from naturally occurring polymers and containing quaternary ammonium groups. The amount of the cationic substance in the composition can vary over broad limits, and depends on the nature of the specific substance and is generally in the range of from 0.1 to 20 wt. % based on the total composition, preferably, from 0.2 to 10 wt. %, and more preferably from 1 to 5 wt. %.

Some substances can play a double role in the compositions of the invention. That is, they can function as a filler and a cationic substance at the same time. Examples of these substances are ion-exchange cross-linked polymers which can be in the form of finely dispersed resins (Amberlite ®, Dowex ®, Cefadex ®, or disintegrated ion-exchange fibers.

The other component of the compositions according to the invention is a radio-opaque substance which provides X-ray visualization of the embolization procedure. Fluorescent substances may also be incorporated in the composition to provide visualization of the embolus. The above mentioned inorganic fillers like powdered tantalum or barium sulfate are very satisfactory as these agents. The other group of substances suitable for the purposes of the present invention are iodinated organic substances commonly used as contrast media in X-ray tests. Examples of such substances are sodium iothalamate, sodium metrizoate, metrizamide and so on. The amount of radioopaque ingredient in the composition depends on the X-ray adsorption by the substance. In general, the amount is in the range of from 2 to 30 wt. % of the total weight of the composition, preferably from 4 to 20 wt. %, and more preferably from 5 to 15 wt. %. The compositions according to the present invention can also be used as drug delivery systems. In such cases they may contain water soluble or water insoluble substances possessing various pharmacologic activities. Examples of these substances are antibiotics, anti-inflammatory agents and anti tumor agents.

The other necessary component of the composition of the present invention is thrombin which promotes clot formation upon contacting the composition with blood. In the case of using the compositions for therapeutic percutaneous embolization in humans, it is preferable to use human thrombin. The amount of thrombin in the composition may vary from 0.5 to 1000 NIH units and higher per gram (1 NIH unit of thrombin is defined as the amount of thrombin required to convert 2.5 nanomoles of fibrinogen to fibrin in 15 seconds).

There are several methods by which the compositions according to the invention can be prepared. One method involves making a viscoelastic gel (the procedures for preparing these gels are described in great detail in U.S. Pat. Nos. 4,582,865, 4,605,691 and 4,636,524) with the above mentioned components other than thrombin.

The mixture thereby obtained may be homogenized by any desirable means and sterilized, e.g., by autoclaving. Then, the sterile preparation of thrombin is dissolved in suitable media, e.g., sterile pyrogen-free 0.15M aqueous sodium chloride and the desired amount of the solution is added to the above mixture which is now ready for use in a therapeutic percutaneous embolization procedure.

Another method involves introducing some of the components of the mixture into the viscoelastic gel during the preparation of the latter. These components include fillers, radio-opaque substances and drugs. The other components and thrombin are then mixed with the gel later, as is described above.

There is another method for the preparation of the compositions according to the present invention. According to this method the viscoelastic gel alone or previously mixed with other components can be lyophilized and then rehydrated in the solution containing the remaining desirable components.

As mentioned above, the viscoelastic composition according to the present invention forms a clot when put in contact with blood. The rate of clot formation and the consistency of the clot depend upon and can be controlled by the nature of each component in the formulation, its concentration in the formulation and the ratios of the various components.

DETAILED DESCRIPTION OF THE INVENTION

The following examples are intended to illustrate the invention without limiting the scope thereof, which is defined solely by the appended claims.

EXAMPLE 1

The viscoelastic gel used in this example was obtained according to the following procedure: 0.57 g of air-dried sodium hylan (NaHY) (water content 15 wt. %) was dissolved in 15 ml of distilled water and left standing overnight. To this solution, 2 ml of 2N aqueous sodium hydroxide were added, the resulting mixture was stirred for 15 minutes and then a solution of 0.11 g of vinyl sulfone (Aldrich Chemical Co., Inc.) in 1.6 ml of water was added to the mixture with vigorous stirring. The mixture was stirred for 10 minutes and then left standing for an additional 50 minutes. The gel thereby formed was placed in 500 ml of distilled water and allowed to swell for 24 hours with slow stirring. The water was then replaced with 500 ml of sterile, 0.15M aqueous sodium chloride. The mixture was stirred another 24 hours and the above procedure was repeated one more time. The swollen gel was then separated from the liquid phase. The polymer concentration in the gel was determined as follows. About 1 g of gel was hydrolyzed with 2 ml of 1N sulfuric acid for about 3 hours at 95°–98° C. The thus obtained clear solution was neutralized upon cooling with 2 ml of 1N sodium hydroxide solution and the glucuronic acid content was determined by the carbazole method (An Automated Method For The Determination of Hexuronic Acids, Analytical Biochemistry, 2, 517–558 (1965)).

The polymer content in the viscoelastic gel was found to be 0.38%. The gel had the following rheological properties: apparent viscosity, 723 Pa.s at shear rate $0.01s^{-1}$; dynamic elastic modulus at 5 Hz, 13.9 Pa, shear dependent plasticity (viscosity ratio at shear rates 0.01 and $15.7s^{-1}$)=250.

1.0 g of the viscoelastic gel was mixed with 0.2 g of a 20% solution of hexamethonium chloride (HMC, Sigma Chemical Co.) in normal saline (0.15M aqueous NaCl) and the mixture was sterilized by autoclaving for 20 minutes. A sterile solution of human thrombin (KABI Helena Laboratories, Beaumont, Texas) in normal saline containing 2.5 NIH units was added to the mixture. Normal whole citrated venous blood (9 parts of blood mixed with one part of 3.8% aqueous sodium citrate) was prepared from human donated blood and used within 24 hours in the clotting assay. Plasma was prepared from whole citrated blood by centrifugation at 2000 rpm (300 g) for 20 minutes at room temperature. The upper plasma layer was carefully removed with a transfer pipet to a clean glass test tube and either used within four hours or frozen at −100° C. until use in the clotting assay. 0.4 g of the above prepared mixture was mixed with 0.4 ml of plasma. A solid clot formed after incubation at 37° C. for 150 seconds. When incubated at 37° C. with whole blood the viscoelastic mixture gave a solid clot within 200 seconds.

EXAMPLE 2

The above experiment was repeated with the exception that 0.06 g of microcrystalline cellulose powder (Sigma Chemical Co.) was added to the viscoelastic mixture. A very strong solid clot started to form with plasma and with whole blood in about 30 seconds and was fully developed in about 100 seconds.

EXAMPLE 3

One gram of the viscoelastic gel prepared as described in Example 1 was mixed with 0.1 g of microcrystalline cellulose, 0.1 g of 20% HMC solution in saline and 0.2 g of barium sulfate and the mixture was sterilized by autoclaving after which 0.5 ml of a thrombin solution containing 2.5 NIH units was added to the mixture. A solid clot formed in about two minutes after incubating the mixture of equal amounts of the embolizing composition and plasma at 37° C.

EXAMPLE 4

One gram of the gel prepared according to Example 1 was mixed with 0.2 g of 20% HMC solution in normal saline and 0.2 g of polypropylene powder with particle size less than 20 μm. To 0.4 g of the autoclaved mixture, a thrombin solution was added in an amount corresponding to 2.5 NIH units and the mixture obtained was mixed with 0.4 ml of a whole blood. A strong clot developed in about 80 seconds at 37° C.

EXAMPLE 5

2.45 g of the gel prepared according to Example 1 were mixed with 0.125 g of anion-exchange resin QAE Sephadex ® (Sigma Chemical Co.). The mixture was autoclaved and mixed with a thrombin solution in an amount corresponding to 2.5 NIH units. When incubated with plasma in a weight ratio of 1:1 the mixture provided the formation of a strong clot in about 10 minutes.

EXAMPLE 6

A viscoelastic gel containing powdered tantalum was prepared in the following manner: one gram of NaHY fibers (water content of about 30%) was mixed with 20 ml of water and allowed to swell overnight. 2.8 ml of a 2M aqueous solution of sodium hydroxide were added to the solution obtained. 10 g of powdered tantalum (particle size about 1 ξm) mixed with 2 ml of water were stirred into the above solution and a solution of 0.2 g of vinyl sulfone in 2 ml of water was added to the obtained suspension. The mixture was energetically stirred by hand until the gelation point occurred, which was about 8 minutes. The gel was left standing for about 1 hour and then was allowed to swell in normal saline overnight. The swollen gel was washed with normal saline 4 more times, each wash being of about 4 hours duration. The polymer content in the gel was determined as described in Example 1, with the exception that after hydrolysis the liquid phase and tantalum were separated by centrifugation and the hexuronic acid content was determined in the solution. The polymer content in the gel was 0.43 wt. %. The tantalum content was determined by weight method and found to be 6.13 wt. %. The rheological properties of the tantalum containing gel were the following: apparent viscosity at shear rate $0.01s^{-1}=3000$ Pa.s; elastic modulus at 5 Hz=70.3 Pa; shear dependent plasticity (ratio of viscosities at shear rates of 0.01 and $14.7s^{-1}$)=457.

One gram of the viscoelastic gel thereby obtained was mixed with 0.06 g of microcrystalline cellulose and 0.1 g of 20% HMC solution in normal saline. The mixture was autoclaved and a thrombin solution in an amount corresponding to 2.5 NIH units was added thereto. The obtained mixture was mixed with plasma in a volume ratio of 1:1 and incubated at 37° C. The clot formation started in about 30 seconds and after about 4 minutes a very tough, solid clot formed. The clotting assay was repeated with whole blood and essentially the same results were obtained but the clotting time was about two times longer.

Figure 2:
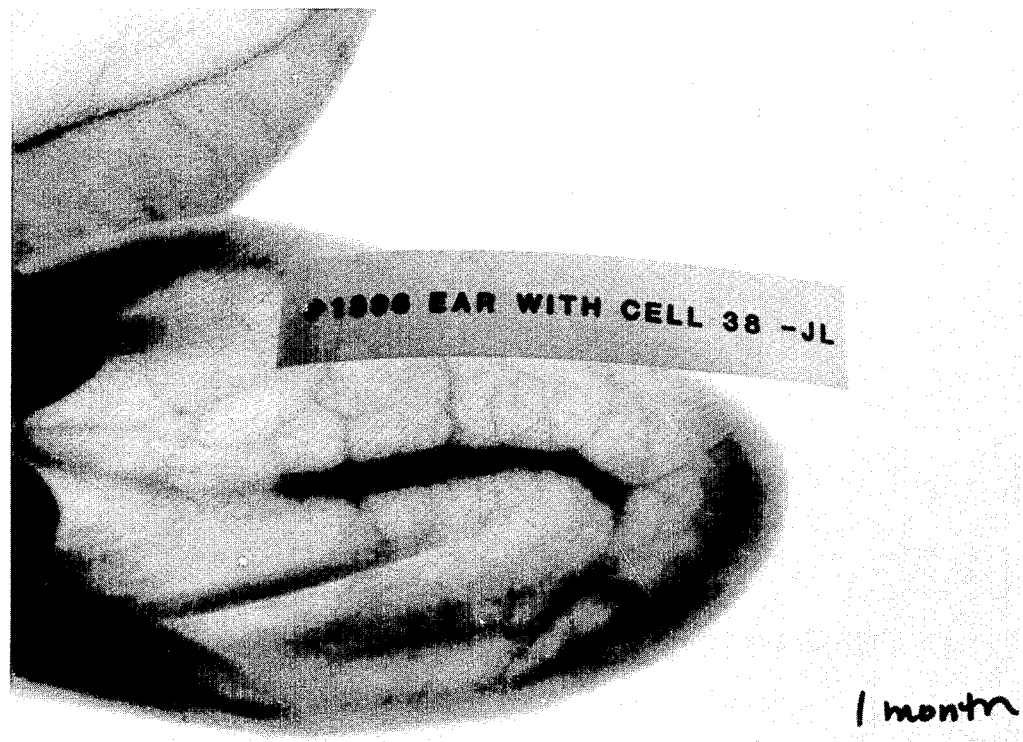
FIG. 2 is a photograph showing the arterially injected ears of a rabbit one month after injection with a composition according to the invention.

The embolizing effect of the mixture was evaluated in vivo as follows:

New Zealand white rabbits (male, SPF, Hazelton, 2-3 Kg weight) were anesthetized with ketamine/rompun. The fur was shaved from areas on the ears in order to facilitate arterial injection. The viscoelastic mixture prepared as described above in this example was injected into the auricular artery (approximately 0.05 cc). The arterially injected gel mixture rapidly formed a firm clot in each injected vessel approximately 4 cm in length and which could be readily visually observed because of the solidification of the vessels and the black color of the mixture caused by the presence of the tantalum which can be seen through the skin. There were no visible changes observed in the occluded arteries after one and after 4 weeks (FIGS. 1 and 2, respectively). Histological examination of cross sections of the auricular arteries of the animals after sacrifice showed that the formed embolism completely occupied the vessels, i.e., there remained no unfilled portion of th vessel.

EXAMPLE 7

One gram of the tantalum containing gel described in the previous example was mixed with 0.06 g of microcrystalline cellulose and 0.1 g of a 20% solution of choline chloride in normal saline. The amount of thrombin added to the mixture corresponded to 2 NIH units. Equal amounts by weight of the gel mixture and plasma were mixed and incubated at 37° C. A very strong clot formed in about 5 minutes.

EXAMPLE 8

A viscoelastic gel having microcrystalline cellulose particles uniformly distributed therein was prepared as is described in Example 6 with the exception that instead of tantalum, 10.0 g of microcrystalline cellulose particles were dispersed in the hylan solution prior to cross-linking. A firm, viscoelastic gel with an HY content of 0.61 wt. % and a cellulose content of about 16% was obtained. One gram of this gel was mixed with 0.1 g of a 20% solution of choline chloride (Aldrich Chemical Co., Inc.) in normal saline and 0.13 g of tantalum powder. Equal parts of the mixture and plasma were mixed and incubated at 37° C. A strong clot formed within about 20 minutes.

EXAMPLE 9

The tantalum containing viscoelastic gel was prepared as described in Example 6. Cross-linked NaHY fibers were prepared as follows: One gram of fibers was put into a mixture containing 66.0 g of acetone, 26.2 g of water, 1 g of concentrated hydrochloric acid and 6.8 g of a 37% formalin solution and the mixture was refluxed for 15 minutes. The fibers were removed from the solution, washed 2 times with acetone/water (2:1 mixture overnight each wash), then washed 2 times with acetone and dried in vacuum. One gram of the viscoelastic gel was mixed with 0.06 g of cross-linked fibers of NaHY (disintegrated in a mortar), 0.1 g of 20% HMC solution in normal saline, and thrombin solution in an amount corresponding to 2.5 NIH units. The mixture obtained was mixed with plasma in equal amounts and a strong clot formed within several seconds at 37° C.

EXAMPLE 10

This example illustrates that thrombin alone mixed with the viscoelastic gel does not provide the desired embolization. One gram of the viscoelastic gel prepared as described in Example 1 was mixed with an amount of thrombin corresponding to 2.5 NIH units. The mixture did not provide clot formation when incubated either with plasma or whole blood at 37° C for more than 60 minutes.

EXAMPLE 11

The tantalum containing viscoelastic gel was prepared as described in Example 6. 0.5 gram of the viscoelastic gel was placed in a glass test tube, and frozen rapidly in an acetone/ dry ice bath. The frozen viscoelastic gel was then lyophilized. The lyophilized viscoelastic gel was rehydrated with 0.22 ml of aqueous solution containing 8 uCi of $^{125}$I-gentamicin antibiotic and 10 NIH units of thrombin. The obtained mixture was mixed with whole citrated human blood in a volume ratio of 1:1 and incubated at 37° C. The clot formation started within 2-3 seconds and was complete within 1 minute. The embolizing and drug delivery effects of the mixture were evaluated in vivo as follows:

New Zealand white rabbits (male, SPF, Hazelton, 2-3 Kg weight) were anesthetized with ketamine/rompun. The fur was shaved from areas on the ears in order to facilitate arterial injection. A 25 microliter venous blood sample was obtained before injection of the mixture. The viscoelastic mixture prepared as described above in this example was injected into the auricular artery (approximately 0.05 cc). The arterially injected gel mixture rapidly formed a firm clot in each injected vessel approximately 4 cm in length and which could be readily visually observed because of the solidification of the vessels and the black color of the mixture caused by the presence of the tantalum which can be seen through the skin. Blood samples (approximately 25 microliters) were taken 1, 2, 3, 4, and 24 hours after injection and the radioactivity in each blood sample was measured in a Packard Gamma counter. Urine was also collected (1, 2 and 3 days). $^{125}$I-gentamicin was detected in the blood taken from the local ear vein more than four hours after injection of the mixture. $^{125}$I-gentamicin was detected in urine at 24 and 48 hours. These results indicate that the antibiotic gentamicin can be combined with the embolizing composition for delivery to the surrounding tissues by the embolized composition.

EXAMPLE 12

The tantalum containing viscoelastic gel was prepared as described in Example 6. 0.5 gram of the viscoelastic gel was mixed with 135 uCi (2.7 μg) of $^{125}$I-histamine ($^{125}$I-histamine was used as a model for drug delivery because of its low molecular weight, high specific activity, and availability), 0.03 g of microcrystalline cellulose, 0.05 g of 20% HMC solution in normal saline, and 10 NIH units of thrombin.

The embolizing effect of the mixture was evaluated in vivo as follows:

New Zealand white rabbits (male, SPF, Hazelton, 2-3 Kg weight) were anesthetized with ketamine/- rompun. The fur was shaved from areas on the ears in order to facilitate arterial injection. The viscoelastic mixture prepared as described above in this example was injected into the auricular artery (approximately 0.05 cc). The arterially injected gel mixture rapidly formed a firm clot in each injected vessel approximately 4 cm in length and which could be readily visually observed because of the solidification of the vessels and the black color of the mixture caused by the presence of the tantalum which can be seen through the skin. Blood samples (approximately 25 microliters) were taken before the injection and 1, 2, 4, and 24 hours after the injection. Urine was collected at 1, 2, and 3 days. Radioactivity in each blood and urine sample was measured in a Packard Gamma counter. $^{125}$I-histamine was detected in the blood for up to 24 hours after injection of the mixture. Radioactivity in the urine was detectable for more than 48 hours after injection. These results indicate that small molecules combined with the embolizing composition are released into the surrounding tissues by the embolized composition and can be combined with the embolizing composition for delivery to the surrounding tissues by the embolized composition.

Variations and modifications can, of course, be made without departing from the spirit and scope of the invention.

Having thus described our invention, what we desire to secure by Letters Patent and hereby claim is:

1. A composition for effecting embolization in blood vessels which comprises a physical mixture of
   (a) a first component which is a cross-linked gel of hyaluronic acid, a cross-linked gel of hylan, or a mixed gel of hyaluronic acid or hylan co-cross-linked with at least one other hydrophilic polymer copolymerizable therewith;
   (b) a cationic organic substance containing quaternary ammonium groups; and
   (c) thrombin.

2. A composition according to claim 1 wherein said at least one other hydrophilic polymer is a natural or synthetic polysaccharide selected from the group consisting of hydroxyethyl cellulose, carboxymethyl cellulose, xanthan gum, chondroitin sulfate and heparin, a protein selected from the group consisting of collagen, elastin, albumin, a globulin, keratin sulfate, a sulfated aminoglycosaminoglycan and a synthetic water soluble polymer.

3. A composition according to claim 1 wherein the cationic organic substance containing quaternary ammonium groups is a monomeric compound containing at least one cationic group selected from the group consisting of choline chloride, acetylcholine chloride and N,N,N,N',N',N'-hexamethyl - 1,6-diaminium bromide, hexadimethrine bromide or a soluble high molecular weight polymer containing quaternary ammonium groups.

4. A composition according to claim 1 wherein the thrombin is human thrombin.

5. A composition according to claim 1 wherein the first component has an apparent viscosity $\eta$ at a shear rate ($\gamma = 0.01 s^{-1}$) of from 10 to several thousands Pa.s; a dynamic storage modulus at 5 Hz of from 10 to 100 Pa; a dynamic loss modulus at 5 Hz of from 5 to 20 Pa; and a pseudoplasticity of from 10 to several thousands.

6. A composition according to claim 1 and further comprising a water insoluble filler.

7. A composition according to claim 6 wherein the water insoluble filler is a hydrophilic, hydrophobic, organic or inorganic material.

8. A composition according to claim 7 wherein the filler is an inorganic material.

9. A composition according to claim 8 wherein the inorganic material is a metal powder or an insoluble salt.

10. A composition according to claim 9 wherein the insoluble salt is barium sulfate.

11. A composition according to claim 7 wherein the filler is an organic material.

12. A composition according to claim 11 wherein the organic material is microcrystalline cellulose, polyethylene, polytetrafluoroethylene, cross-linked hyaluronic acid, agarose or an ion-exchange resin.

13. A composition according to claim 1 and further comprising a radio-opaque substance.

14. A composition according to claim 13 wherein the radio-opaque substance is an inorganic filler selected from the group consisting of powdered tantalum and barium sulfate.

15. A composition according to claim 13 wherein the radio-opaque substance is an iodinated organic substance.

16. A composition according to claim 15 wherein the iodinated organic substance is sodium iothalamate, sodium metrizoate or metrizamide.

17. A composition according to claim 1 wherein the cationic organic substance comprises from 0.1 to 20% by weight of the total weight and the composition contains from 0.5 to 1000 NIH units of thrombin per gram of the composition.

18. A composition according to claim 17 wherein the cationic organic substance comprises from 0.2 to 10% by weight.

19. A composition according to claim 18 wherein the cationic organic substance comprises from 1 to 5% by weight.

20. A composition according to claim 6 wherein the water insoluble filler comprises from 1 to 60% by weight of the total weight of the composition.

21. A composition according to claim 20 wherein the water insoluble filler comprises from 2 to 30% by weight.

22. A composition according to claim 21 wherein the water insoluble filler comprises from 5 to 25% by weight.

23. A composition according to claim 13 wherein the radio-opaque substance comprises from 2 to 30% by weight of the total weight of the composition.

24. A composition according to claim 23 wherein the radio-opaque substance comprises from 4 to 20% by weight.

25. A composition according to claim 24 wherein the radio-opaque substance comprises from 5 to 15% by weight.

26. A composition according to claim 1 and further comprising a fluorescent substance.

27. A method for producing a therapeutic embolus in vivo in an animal comprising intraarterially injecting into an animal an effective amount of a composition as claimed in claim 1.

28. A method for treating a tumor comprising producing an embolus in accordance with the method according to claim 26 at a point upstream of where an artery enters the tumor to be treated, thereby depriving the tumor of nutrients otherwise supplied thereto by said artery.

29. A drug delivery system comprising a composition according to claim 1 and an effective amount of a drug to be delivered from an embolus formed in vivo from the composition.

* * * * *